(12) United States Patent
Amano et al.

(10) Patent No.: US 8,058,471 B2
(45) Date of Patent: Nov. 15, 2011

(54) METHOD FOR PRODUCING OPTICALLY ACTIVE HYDROXYCARBOXYLIC ACID DERIVATIVES OR SALTS THEREOF

(75) Inventors: Susumu Amano, Takasago (JP); Akio Fujii, Takasago (JP); Shohei Yamamoto, Takasago (JP); Masaru Mitsuda, Takasago (JP)

(73) Assignee: Kaneka Corporation, Kita-ku, Osaka-shi (JP)

( * ) Notice: Subject to any disclaimer, the term of this patent is extended or adjusted under 35 U.S.C. 154(b) by 239 days.

(21) Appl. No.: 12/376,803

(22) PCT Filed: Aug. 8, 2007

(86) PCT No.: PCT/JP2007/065559
§ 371 (c)(1),
(2), (4) Date: Apr. 9, 2009

(87) PCT Pub. No.: WO2008/018520
PCT Pub. Date: Feb. 14, 2008

(65) Prior Publication Data
US 2010/0191011 A1    Jul. 29, 2010

(30) Foreign Application Priority Data
Aug. 9, 2006  (JP) .................................. 2006-216771

(51) Int. Cl.
*C07C 59/00* (2006.01)
*C07C 65/21* (2006.01)
(52) U.S. Cl. ..................................................... 562/470
(58) Field of Classification Search .......................... None
See application file for complete search history.

(56) References Cited

U.S. PATENT DOCUMENTS

| | | | |
|---|---|---|---|
| 4,614,806 A | 9/1986 | Buzby, Jr. et al. | |
| 5,066,815 A | 11/1991 | Sayo et al. | |
| 5,686,275 A | 11/1997 | Casey et al. | |
| 6,284,925 B1 | 9/2001 | Knochel et al. | |
| 2003/0004362 A1 | 1/2003 | Tada et al. | |

FOREIGN PATENT DOCUMENTS

| | | |
|---|---|---|
| JP | 63-316744 | 12/1988 |
| JP | 7-502410 | 3/1995 |
| JP | 9-157196 | 6/1997 |
| JP | 10-120621 | 5/1998 |
| JP | 2000-053593 | 2/2000 |
| JP | 2001-199928 | 7/2001 |
| JP | 2003-034665 | 2/2003 |
| WO | WO-2005-049816 | 6/2005 |

OTHER PUBLICATIONS

Ikariya et al. (Derwent abstract of JP 2001199928).*
Spitaleri et al. (Inorganica Chimica Acta, 2003, 352, 61-71).*
Ogo et al. (Organometallics, 2002, 21, 2964-2969).*
Eduardo M. Rustoy, et al.; "Combination strategy using pure enzymes and whole cells as biocatalysts for the preparation of 2-hydroxyesters and lactones from 2-oxoglutaric acid"; Eduardo M. Rustoy, et al.; Tetrahedron: Asymmetry 15 (2004) 3763-3768.
Zhe Wang et al.; "Enantioselective Synthesis of α-Hydroxy Carboxylic Acids: Direct Conversion of α-Oxocarboxylic Acids to Enantiomerically Enriched α-Hydroxy Carboxylic Acids via Neighboring Group Control"; Zhe Wang et al.; Tetrahedron Letters 39 (1998) 5501-5504.
Felix Spindler et al; "A Highly Enantioselective Rhodium Catalyst for the Hydrogenation of Aliphatic α-Keto Esters"; Felix Spindler et al; CHIRALITY 3:370-375 (1991).
English translation of International Preliminary Report on Patentability (Chapter I) issued in related International Application No. PCT/JP2007/065559 on Mar. 10, 2009.

* cited by examiner

*Primary Examiner* — Daniel Sullivan
*Assistant Examiner* — Jennifer C Sawyer
(74) *Attorney, Agent, or Firm* — Connolly Bove Lodge & Hutz LLP

(57) ABSTRACT

The present invention has its object to provide a method for producing an optically active hydroxycarboxylic acid derivative which is an intermediate important for production of medicines, agrochemicals, chemical products, and so on. The production method of the present invention comprises: carrying out a hydrogen-transfer reduction of a ketocarboxylic acid or a salt thereof by the reaction of an optically active diamine complex to produce an optically active hydroxycarboxylic acid derivative. According to the present invention, it is possible to safely and efficiently produce an industrially-useful optically active hydroxycarboxylic acid derivative.

8 Claims, No Drawings

METHOD FOR PRODUCING OPTICALLY ACTIVE HYDROXYCARBOXYLIC ACID DERIVATIVES OR SALTS THEREOF

CROSS REFERENCE TO RELATED APPLICATIONS

This application is a National Stage of PCT/JP2007/065559 filed Aug. 8, 2007 which in turn claims priority from Japanese Application 2006-216771 filed Aug. 9, 2006, the entire contents of which are incorporated herein by reference.

TECHNICAL FIELD

The present invention relates to a method for producing optically active hydroxycarboxylic acid derivatives suitable for general use. Optically active hydroxycarboxylic acid derivatives are intermediates important for the production of medicines, agrochemicals, chemical products, and so on.

BACKGROUND ART

It is generally difficult to asymmetrically reduce ketocarboxylic acid derivatives represented by the general formula (1):

[Chem. 1]

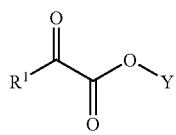
(1)

(in the formula, $R^1$ is an optionally substituted alkyl group having 1 to 20 carbon atoms; Y is hydrogen or a metal) or salts thereof. For this reason, only the following methods are known as methods for producing optically active hydroxycarboxylic acid derivatives represented by the general formula (3):

[Chem. 2]

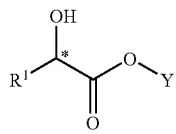
(3)

(in the formula, $R^1$ and Y are the same as described above, and * represents an asymmetric carbon).

(i) A method using an enzyme (Non-Patent Document 1, Patent Document 1).

(ii) A method using a stoichiometric amount of optically active reagent:
 (a) a method using an optically active reducing reagent (Non-Patent Document 2);
 (b) a method using an optically active ligand (Patent Document 2).

(iii) A method using a catalytic amount of optically active reagent:
 (a) a method using hydrogen gas and a transition metal reagent (Non-Patent Document 3).

Patent Document 1: WO 2005/049816
Patent Document 2: U.S. Pat. No. 4,614,806
Non-Patent Document 1: Tetrahedron: Asymmetry, 2004, 15(23), 3763.
Non-Patent Document 2: Tetrahedron Letters, 1998, 39, 5501.
Non-Patent Document 3: Chirality, 1991, 3(4), 370.

However, compounds that can be used in the production method (i) are limited, and this method cannot be generally used. Furthermore, the productivity of this method is typically low and there is a problem in industrial use.

In the production method (ii), an expensive optically active reagent has to be used in an amount equivalent to that of a reaction substrate and there is a problem in industrial use.

In the production method (iii), because hazardous hydrogen gas is used and a very expensive transition metal catalyst is used, there is a problem in industrial use.

SUMMARY OF THE INVENTION

With the foregoing in view, it is an object of the present invention to efficiently produce optically active hydroxycarboxylic acid derivatives that are important for production of medicines and so on from various ketocarboxylic acid derivatives or salts thereof.

That is, the present invention relates to a method for producing an optically active hydroxycarboxylic acid derivative represented by the above general formula (3) or a salt thereof, and the method comprises: carrying out a hydrogen-transfer reduction of a ketocarboxylic acid derivative represented by the above general formula (1) or a salt thereof in the presence of a hydrogen donor compound and an optically active diamine complex represented by the general formula (2):

[Chem. 3]

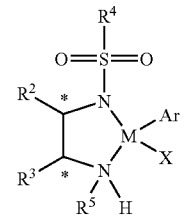
(2)

(in the formula, each of $R^2$ and $R^3$ represents an optionally substituted alkyl group having 1 to 20 carbon atoms or an optionally substituted aryl group having 6 to 14 carbon atoms; $R^4$ represents an optionally substituted alkyl group having 1 to 20 carbon atoms or an optionally substituted aryl group having 6 to 14 carbon atoms; $R^5$ represents an optionally substituted alkyl group having 1 to 20 carbon atoms, an optionally substituted aryl group having 6 to 14 carbon atoms, or hydrogen; Ar represents an optionally substituted aromatic compound; M represents a transition metal; X represents a halogen atom; and * represents an asymmetric carbon).

By performing a hydrogen-transfer reduction that can be generally used, as in the method according to the present invention, it is possible to simply produce optically active hydroxycarboxylic acid derivatives or salts thereof that are important for production of various products, for example in the field of medicines, from various ketocarboxylic acid derivatives or salts thereof.

BEST MODE FOR CARRYING OUT THE INVENTION

In the present invention, a reduction reaction is performed by a hydrogen-transfer reduction. In the hydrogen-transfer reduction, a hydrogen atom is transferred from a hydrogen donor compound to a substrate to reduce the substrate. A compound that can be easily handled, such as an acid or an alcohol, is used as the hydrogen donor compound, and hazardous hydrogen gas or a metal hydride reagent having poor handleability that are generally used in reduction are not used. Further, the reaction can proceed under mild conditions and requires no special equipment.

Further, in the present invention, an optically active diamine complex represented by the formula (2) is used upon the reduction. By contrast with the usual transition metal catalysts, the optically active diamine complex represented by the formula (2) is easy to handle because it is stable to moisture, oxygen, and so on and does not require stringent removal of moisture and oxygen upon the reaction. Furthermore, this complex can be obtained at a low cost because it can be synthesized from generally used diamines.

In the present description, examples of the optionally substituted alkyl group having 1 to 20 carbon atoms that are represented by $R^1$ to $R^5$ include a methyl group, an ethyl group, an n-propyl group, an isopropyl group, an n-butyl group, an isobutyl group, a sec-butyl group, a tert-butyl group, an n-pentyl group, an isopentyl group, an n-hexyl group, an n-octyl group, a cyclopentyl group, a cyclohexyl group, a hydroxymethyl group, a chloromethyl group, a benzyl group, an o-, m-, or p-nitrobenzyl groups, a p-chlorobenzyl group, a 4-methylbenzyl group, a 3-methylbenzyl group, a 2-methylbenzyl group, a 4-methoxybenzyl group, a 3-methoxybenzyl group, a 2-methoxybenzyl group, a 1-phenylethyl group, a 2-phenylethyl group, a 1-(4-methylphenyl)ethyl group, a 1-(4-methoxyphenyl)ethyl group, a 3-phenylpropyl group, a 2-phenylpropyl group, and so on. Examples of substituents include an alkyl group, an aryl group, an amino group, a nitro group, a sulfonyl group, a halogen atom, a hydroxyl group, an alkoxyl group, and so on, but the substituents are not limited to these examples.

Examples of the optionally substituted aryl groups having 6 to 14 carbon atoms that are represented by $R^2$ to $R^5$ include a phenyl group, a p-hydroxyphenyl group, a 1-naphthyl group, a 2-naphthyl group, a 4-methylphenyl group, a 3-methylphenyl group, a 2-methylphenyl group, a 4-ethylphenyl group, a 3-ethylphenyl group, a 4-methoxyphenyl group, a 3-methoxyphenyl group, a 2-methoxyphenyl group, a 4-nitrophenyl group, a 4-phenylphenyl group, a 4-chlorophenyl group, a 4-bromophenyl group, and so on. Examples of substituents include the above-listed substituents, but the substituents are not limited to these examples.

The number of carbon atoms as referred to herein does not include the number of carbon atoms in a substituent.

The present invention will be described below in more detail.

The production method according to the present invention comprises: carrying out a hydrogen-transfer reduction of a ketocarboxylic acid derivative represented by the general formula (1):

[Chem. 4]

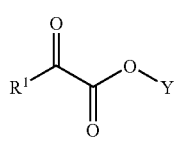

(1)

or a salt thereof in the presence of a hydrogen donor compound and an optically active diamine complex represented by the general formula (2):

[Chem. 5]

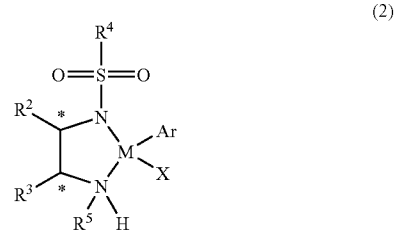

(2)

to prepare an optically active hydroxycarboxylic acid derivative represented by the general formula (3).

[Chem. 6]

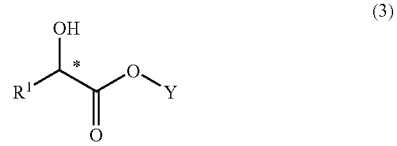

(3)

In the above formulas (1) and (3), $R^1$ represents an optionally substituted alkyl group having 1 to 20 carbon atoms.

Preferred examples of $R^1$ include a methyl group, an ethyl group, an isopropyl group, a tert-butyl group, an n-octyl group, a hydroxymethyl group, a chloromethyl group, a benzyl group, an o-, m-, or p-nitrobenzyl group, a 2-phenylethyl group, and so on, but $R^1$ is not limited to these examples. More preferred examples include a methyl group, an ethyl group, an isopropyl group, a tert-butyl group, an n-octyl group, a hydroxymethyl group, a chloromethyl group, a benzyl group, an o-, m-, or p-nitrobenzyl group, and a 2-phenylethyl group.

In the above formulas (1) and (3), Y represents hydrogen or a metal atom. Specific examples of metal atoms include: alkali metals such as lithium, sodium, and potassium; alkaline earth metals such as magnesium and calcium; halogenated earth metals such as magnesium chloride and calcium chloride; aluminum; and so on, but Y is not limited to these examples. Y is preferably hydrogen, an alkali metal, an alkaline earth metal, or a halogenated earth metal, and hydrogen is more preferred among these.

In the formula (1), a ketocarboxylic acid derivative with Y being hydrogen can be similarly used in the form of a ketocarboxylic acid salt formed with an amine. Specific examples of amines include ammonia, methylamine, ethylamine, phenylethylamine, diisopropylamine, triethylamine, aniline, lutidine, and so on, but amines are not limited to these examples.

In the formula (2), each of $R^2$ and $R^3$ is an optionally substituted alkyl group having 1 to 20 carbon atoms or an optionally substituted aryl group having 6 to 14 carbon atoms. $R^2$ and $R^3$ may be same or different, and may form a ring together. Preferred examples of $R^2$ and $R^3$ include a methyl group, an ethyl group, an isopropyl group, a tert-butyl group, an n-octyl group, a hydroxymethyl group, a chloromethyl group, a phenyl group, a p-hydroxyphenyl group, a benzyl group, an o-, m-, or p-tolyl group, an o-, m-, or p-anisyl group, a p-chlorobenzyl group, a naphthyl group, a tetramethylene group, and so on, but the $R^2$ and $R^3$ are not limited to these examples. It is more preferred that $R^2$ and $R^3$ be both phenyl groups or that $R^2$ and $R^3$ together form a cyclic tetramethylene group.

In the formula (2), $R^4$ is an optionally substituted alkyl group having 1 to 20 carbon atoms or an optionally substituted aryl group having 6 to 14 carbon atoms.

Preferred examples of $R^4$ include a methyl group, an ethyl group, an isopropyl group, a tert-butyl group, an n-octyl group, a hydroxymethyl group, a chloromethyl group, a trifluoromethyl group, a benzyl group, a phenyl group, a p-hydroxyphenyl group, an o-, m-, or p-nitrophenyl group, an o-, m-, or p-tolyl group, an o-, m-, or p-trifluoromethylphenyl group, a p-chlorobenzyl group, a 2,4,6-trimethylphenyl group, a 2,4,6-triisopropylphenyl group, a 6-trimethoxyphenyl group, a naphthyl group, a 2,4,6-trichlorophenyl group, and so on, but $R^4$ is not limited to these examples. It is more preferred that $R^4$ be a methyl group, a trifluoromethyl group, a phenyl group, a p-tolyl group, a p-trifluoromethylphenyl group, or a 2,4,6-trichlorophenyl group. A p-tolyl group is particularly preferred among these.

In the formula (2), $R^5$ is an optionally substituted alkyl group having 1 to 20 carbon atoms, an optionally substituted aryl group having 6 to 14 carbon atoms, or hydrogen. Preferred examples of $R^5$ include hydrogen, a methyl group, an ethyl group, an isopropyl group, a tert-butyl group, an n-octyl group, a hydroxymethyl group, a chloromethyl group, a phenyl group, a p-hydroxyphenyl group, a benzyl group, a p-chlorobenzyl group, a naphthyl group, and so on, but $R^5$ is not limited to these examples. It is more preferred that $R^5$ be hydrogen or a methyl group. Hydrogen is particularly preferred among these.

In the formula (2), Ar represents an optionally substituted aromatic compound. Specific examples thereof include benzene, toluene, xylene, mesitylene, hexamethylbenzene, ethylbenzene, tert-butylbenzene, p-cymene, cumene, pentamethylcyclopentadienyl, and so on, but Ar is not limited to these examples. It is preferred that Ar be p-cymene, benzene, mesitylene, or pentamethylcyclopentadienyl. More preferred is p-cymene.

Further, in the formula (2), M represents a transition metal. Specific examples thereof include palladium, rhodium, ruthenium, iridium, platinum, zirconium, titanium, chromium, cobalt, copper, nickel, zinc, manganese, iron, ytterbium, lanthanum, and so on, but M is not limited to these examples. It is preferred that M is ruthenium, rhodium, and iridium. Ruthenium is more preferred.

Further, in the formula (2), X is a halogen atom. Specific examples thereof include fluorine, chlorine, bromine, iodine, and so on. Chlorine is preferred.

Further, in the formula (2) above, * represents an asymmetric carbon. The configuration of each of asymmetric carbon atoms may be (R) or (S). In the case that both $R^2$ and $R^3$ are phenyl groups or in the case that $R^2$ and $R^3$ together form a cyclic tetramethylene group, it is preferred that both be (R) or both be (S).

Also, in the formula (3), * represents an asymmetric carbon. The configuration of an asymmetric carbon atom may be (R) or (S).

The amount of optically active diamine complex represented by the formula (2) used in the present hydrogen-transfer reduction process is not particularly limited, but the amount is usually 0.00001 to 1 equivalent, preferably 0.0001 to 0.1 equivalent, even more preferably 0.0001 to 0.01 equivalent to that of the ketocarboxylic acid represented by the formula (1) or the ketocarboxylic acid salt.

The hydrogen donor compound used in the present process is not particularly limited, but an alcohol, formic acid, or a formic acid salt is preferred.

Specific examples of alcohols include methanol, ethanol, n-propanol, isopropanol, and so on, but the alcohols are not limited to these examples. Isopropanol is preferred.

Examples of the formic acid salt include sodium formate and ammonium formate, but the formic acid salt is not limited to these examples.

The preferred hydrogen donor compound is formic acid or isopropanol, and formic acid is more preferred.

It is preferred that the reaction of the present process is carried out in the coexistence of a base. Examples of bases include organic amines, inorganic bases, and so on. Specific examples of inorganic bases include sodium hydroxide, potassium hydroxide, potassium carbonate, and so on, but the inorganic bases are not limited to these examples. Specific examples of organic amines include trimethylamine, triethylamine, ammonia, and so on, but the organic amines are not limited to these examples. A combination of formic acid and triethylamine is most preferred among the combinations of hydrogen donor compounds and bases.

The amount of hydrogen donor compound used in the present process is not particularly limited. For example, in the case of formic acid, the amount is usually 1 to 100 equivalents, preferably 1 to 10 equivalents, and more preferably 1 to 3 equivalents to that of the compound represented by the formula (1).

The amount of amine used in the present process is also not particularly limited. For example, in the case of triethylamine, the amount is usually 0.01 to 100 equivalents, preferably 0.1 to 10 equivalents, and more preferably 1 to 4 equivalents to that of the compound represented by the formula (1).

This process does not require a reaction solvent, and it is preferred that the reaction be carried out without a solvent because such a reaction can be completed within a short period of time and the equivalent of catalyst used can be reduced. However, a reaction solvent may be used. In the case that a reaction solvent is used, the type thereof is not particularly limited. A reaction solvent used for the reaction is water, an organic solvent, or a mixed solvent of water and an organic solvent.

The organic solvent is not particularly limited. Examples thereof include: alcohol solvents such as methanol, ethanol, butanol, isopropanol, ethylene glycol, and methoxy alcohol; hydrocarbon solvents such as benzene, toluene, n-hexane, and cyclohexane; ether solvents such as diethyl ether, tetrahydrofuran, 1,4-dioxane, methyl t-butyl ether, dimethoxyethane, and ethylene glycol dimethyl ether; ester solvents such as ethyl acetate and butyl acetate; ketone solvents such as acetone and methyl ethyl ketone; halogen solvents such as methylene chloride, chloroform, and 1,1,1-trichloroethane; nitrogen-containing solvents such as acetonitrile, acetamide, and dimethylformamide; and aprotic polar solvents such as dimethylsulfoxide, dimethylacetamide, N-methylpyrrolidone, and hexamethylphosphoric triamide. These solvents may be used individually or in combination of two or more thereof.

It is preferred that no solvent be used or that an alcohol solvent, a hydrocarbon solvent, an ether solvent, an ester solvent, a ketone solvent, a halogen solvent, and an aprotic polar solvent be used. It is particularly preferred that no solvent be used or an alcohol solvent be used because the reaction product has high optical purity. It is even more preferred that no solvent be used or that methanol be used.

In the case that a reaction solvent is used, the concentration thereof is not particularly limited, and the concentration at which the compound represented by the formula (1) is charged into the solvent is preferably 40% or less, more preferably 30% or less, and even more preferably 20% or less. The lower limit is not particularly limited, and the preferred lower limit is 5% or more. In the case that the reaction solvent is used, a lower concentration is preferred, but in the case that no solvent is used, contrary to what is described above, a compound represented by the formula (3) can be unexpectedly obtained with high stereoselectivity.

The reaction temperature is preferably −40° C. to 160° C., and more preferably −20° C. to 100° C. Particularly preferred temperature is 0° C. to 60° C.

The reaction procedure in the present process is not particularly limited. Thus, the addition sequence of the compounds represented by the formulas (1) and (2) and hydrogen donor compound is not particularly restricted, but it is preferred that a hydrogen donor compound be added to a mixture of compounds represented by the formulas (1) and (2). Further, when a base coexists, a hydrogen donor compound may be mixed with a base and then added to the mixture of compounds represented by the formulas (1) and (2), but it is preferred that the hydrogen donor compound be added after the base have been added to the mixture of compounds represented by the formulas (1) and (2). The hydrogen donor compound is added all together to allow the reaction to proceed, or is continuously or intermittently added to allow the reaction to proceed. However, from the standpoint of safety, it is preferred that the hydrogen donor compound be added gradually as the reaction proceeds. When the hydrogen donor compound is added continuously or intermittently, the time period required to add the compound is not particularly limited, but it is preferred that the hydrogen donor compound be added at a rate that enables safe discharge of the gas generated as the reaction proceeds. The time period required to add the entire amount is preferably 30 minutes or more, and more preferably 1 hour or more.

The optically active diamine complex represented by the formula (2) may be prepared in advance and an isolated and purified compound may be used, or the complex may be prepared in the system and used.

After the reaction is completed, the obtained reaction mixture may be subjected to a subsequent process, but it is acceptable to perform only a typical after-treatment for obtaining the product from the reaction mixture. For example, after the reaction is completed, pH of the reaction mixture is adjusted if necessary and an extraction operation is performed using a typical extraction solvent such as ethyl acetate, diethyl ether, methylene chloride, toluene, and hexane. The reaction solvent and extraction solvent are distilled off from the obtained extraction mixture by an operation such as vacuum heating to obtain the target product. Also, immediately after the reaction is completed, the reaction solvent may be removed by an appropriate operation such as vacuum heating and then a similar operation may be performed, or water may be added if necessary and then the reaction solvent may be distilled off. Alternatively, after the reaction is completed, at a predetermined temperature, pH of the reaction mixture may be adjusted and the precipitated crystals may be filtrated.

The target product thus obtained is almost pure, but additional purification may be performed to further increase the purity by typically employed methods such as crystallization purification, fractional distillation, column chromatography, and so on. The target product obtained may be dried by using a drier or the like.

A solvent used for crystallization depends on a compound, and therefore, is not particularly limited. Examples of solvents include pentane, hexane, heptane, octane, water, methanol, ethanol, n-propanol, isopropanol, n-butanol, isobutanol, t-butanol, benzene, xylene, trimethylbenzene, tetrahydrofuran, tetrahydropyran, 1,3-dioxane, 1,4-dioxane, methyl acetate, ethyl acetate, n-propyl acetate, isopropyl acetate, n-butyl acetate, isobutyl acetate, t-butyl acetate, dimethyl ether, t-butylmethyl ether, acetonitrile, propionitrile, butyronitrile, acetone, dimethylsulfoxide, dimethylacetamide, N-methylpyrrolidone, mixtures of two or more thereof, and so on.

EXAMPLES

The present invention will be described below in more detail with reference to examples, but the present invention is not limited to the examples.

Example 1

(2R)-hydroxy-3-(o-nitrophenyl) propanoic acid

[Chem. 7]

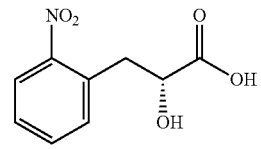

Into 120 ml of methanol were dissolved 293 mg (0.5 mmol) of [RuCl$_2$(p-cymene)]$_2$ and 360 mg (1.0 mmol) of (1R,2R)—N-tosyl-diphenylethylenediamine (hereinafter referred to as (R,R)-TsDPEN) to prepare a solution, and 0.27 ml (2.0 mmol) of triethylamine was dropwise added to the solution, followed by stirring for 0.5 hour at room temperature. To the reaction solution was dropwise added a solution prepared by dissolving 20 g (96 mmol) of o-nitrophenyl pyruvic acid into 80 ml of methanol, and 38.7 g (383 mmol) of triethylamine was furthermore dropwise added thereto. The bath was heated up to a temperature of 40° C., and then 13.2 g (278 mmol) of formic acid was dropwise added over 1 hour, followed by stirring for 2 hours at a bath temperature of 40° C. Upon completion of the reaction, the solvent was distilled off under reduced pressure. Thereto was added 40 ml of water, and then 22.6 g of concentrated hydrochloric acid was gradually dropwise added under ice cooling; thus, pH of the solution was adjusted to 2. Extraction was performed twice with 200 ml of ethyl acetate, and then the organic layer was washed with 20 ml of a saturated aqueous solution of sodium chloride, followed by concentration under reduced pressure. As a result, 27.0 g (yield 97%, 97% ee) of (2R)-hydroxy-3-(o-nitrophenyl)propanoic acid was obtained.

$^1$H-NMR (400 MHz, DMSO-d$_6$): δ 7.90-7.89 (1H, m), 7.65-7.61 (1H, m), 7.51-7.46 (1H, m), 4.17-4.14 (1H, m) 3.33-3.02 (2H, m).

Example 2

(2S)-hydroxy-3-(o-nitrophenyl)propanoic acid

Into 0.27 ml (19 mmol) of triethylamine was dissolved 3 mg (0.0048 mmol) of [RuCl((S,S)-TsDPEN)(p-cymene)] to prepare a solution, and to the solution were added 1.0 g (4.8 mmol) of o-nitrophenyl pyruvic acid and 0.54 ml (14 mmol) of formic acid, followed by stirring for 2 hours at a bath temperature of 40° C. Upon completion of the reaction, the solvent was distilled off under reduced pressure. Thereto was added 2 ml of water, and then 1 g of concentrated hydrochloric acid was gradually dropwise added under ice cooling, and pH of the solution was adjusted to 2. Extraction was performed twice with 10 ml of ethyl acetate, and then the organic phase was washed with 2 ml of a saturated aqueous solution of sodium chloride, followed by concentration under reduced pressure. As a result, 1.4 g (yield 97%, 95% ee) of (2S)-hydroxy-3-(o-nitrophenyl)propanoic acid was obtained.

Example 3

(2R)-hydroxy-3-phenylpropanoic acid

[Chem. 8]

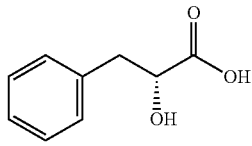

Into 1 ml of methanol were dissolved 7 mg (0.01 mmol) of [RuCl$_2$(p-cymene)]$_2$ and 8 mg (0.02 mmol) of (R,R)-TsDPEN to prepare a solution, and to the solution was dropwise added 2 mg (0.02 mmol) of triethylamine, followed by stirring for 0.5 hour at room temperature. To the reaction solution was dropwise added a solution prepared by dissolving 364 mg (2.2 mmol) of phenylpyruvic acid into 4 ml of methanol, and 1.2 ml (8.9 mmol) of triethylamine was furthermore dropwise added thereto. The bath was heated up to a temperature of 40° C., and then 0.25 ml (6.7 mmol) of formic acid was dropwise added over 1 hour, followed by stirring for 2 hours at a bath temperature of 40° C. Upon completion of the reaction, the solvent was distilled off under reduced pressure. Thereto was added 2 ml of water, and then concentrated hydrochloric acid was gradually dropwise added under ice cooling; thus, pH of the solution was adjusted to 2. Extraction was performed twice with 20 ml of ethyl acetate, and then the organic phase was washed with 2 ml of a saturated aqueous solution of sodium chloride, followed by concentration under reduced pressure. As a result, 370 mg (yield 99%, 94% ee) of (2R)-hydroxy-3-phenylpropanoic acid was obtained.

$^1$H-NMR (400 MHz, CDCl$_3$): δ 7.36-7.24 (5H, m), 4.54-4.51 (1H, m), 3.24-2.98 (2H, m).

Example 4

(2R)-hydroxy-4-phenylbutanoic acid

[Chem. 9]

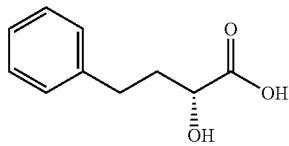

Into 1 ml of methanol were dissolved 7 mg (0.01 mmol) of [RuCl$_2$(p-cymene)]$_2$ and 8 mg (0.02 mmol) of (R,R)-TsDPEN to prepare a solution, and to the solution was dropwise added 2 mg (0.02 mmol) of triethylamine, followed by stirring for 0.5 hour at room temperature. To the reaction solution were dropwise added a solution prepared by dissolving 396 mg (2.2 mmol) of 2-oxo-4-phenylbutanoic acid into 4 ml of methanol, and 1.2 ml (8.9 mmol) of triethylamine was furthermore dropwise added thereto. The bath was heated up to a temperature of 40° C., and then 0.25 ml (6.7 mmol) of formic acid was dropwise added over 1 hour, followed by stirring for 2 hours at a bath temperature of 40° C. Upon completion of the reaction, the solvent was distilled off under reduced pressure. Thereto was added 2 ml of water, and then concentrated hydrochloric acid was gradually dropwise added under ice cooling; thus, pH of the solution was adjusted to 2. Extraction was performed twice with 20 ml of ethyl acetate, and then the organic phase was washed with 2 ml of a saturated aqueous solution of sodium chloride, followed by concentration under reduced pressure. As a result, 509 mg (yield 99%, 85% ee) of (2R)-hydroxy-4-phenylbutanoic acid was obtained. $^1$H-NMR (400 MHz, DMSO-d$_6$): δ 7.28-7.14 (5H, m), 3.91-3.88 (1H, m), 2.66-2.62 (2H, m), 1.91-1.77 (2H, m).

The invention claimed is:

1. A method for producing an optically active hydroxycarboxylic acid derivative represented by the general formula (3):

[Chem. 1]

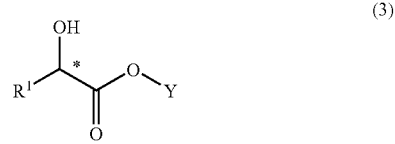

(wherein, R$^1$ represents an optionally substituted alkyl group having 1 to 20 carbon atoms; Y represents hydrogen or a metal atom; and * represents an asymmetric carbon atom) or a salt thereof, the method comprising: carrying out a hydrogen-transfer reduction of a ketocarboxylic acid derivative represented by the general formula (1):

[Chem. 2]

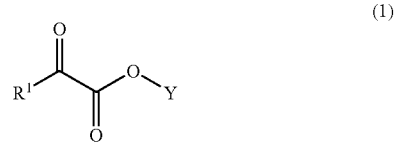

(wherein, R$^1$ and Y are the same as mentioned above) or a salt thereof in the presence of a hydrogen donor compound and an optically active diamine complex represented by the general formula (2):

[Chem. 3]

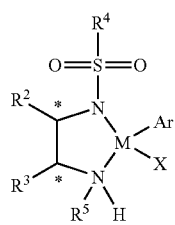

(2)

(wherein, $R^2$ and $R^3$ may be the same or different, each representing an optionally substituted alkyl group having 1 to 20 carbon atoms or an optionally substituted aryl group having 6 to 14 carbon atoms; $R^4$ represents an optionally substituted alkyl group having 1 to 20 carbon atoms or an optionally substituted aryl group having 6 to 14 carbon atoms; $R^5$ represents an optionally substituted alkyl group having 1 to 20 carbon atoms, an optionally substituted aryl group having 6 to 14 carbon atoms, or hydrogen; Ar represents an optionally substituted aromatic compound; M represents a transition metal; X represents a halogen atom; and * is the same as mentioned above, wherein the reaction is carried out in an alcohol solvent or without a solvent.

2. The production method according to claim 1, wherein Y is hydrogen.

3. The production method according to claim 1, wherein formic acid is used as the hydrogen donor compound.

4. The production method according to claim 1, wherein the reaction is carried out in the coexistence of a base.

5. The production method according to claim 2, wherein formic acid is used as the hydrogen donor compound.

6. The production method according to claim 2, wherein the reaction is carried out in the coexistence of a base.

7. The production method according to claim 3, wherein the reaction is carried out in the coexistence of a base.

8. The production method according to claim 5, wherein the reaction is carried out in the coexistence of a base.

* * * * *